(12) United States Patent
Umapathy et al.

(10) Patent No.: US 9,606,062 B2
(45) Date of Patent: Mar. 28, 2017

(54) METHOD AND A SYSTEM FOR DETECTION OF HAZARDOUS CHEMICALS IN A NON-METALLIC CONTAINER

(71) Applicant: INDIAN INSTITUTE OF SCIENCE, Karnataka (IN)

(72) Inventors: Siva Umapathy, Bangalore (IN); Sanchita Sil, West Bangalore (IN); John Kiran, Arakalagudu (IN)

(73) Assignee: INDIAN INSTITUTE OF SCIENCE, Bangalore (IN)

( * ) Notice: Subject to any disclaimer, the term of this patent is extended or adjusted under 35 U.S.C. 154(b) by 0 days.

(21) Appl. No.: 14/374,928

(22) PCT Filed: Sep. 2, 2013

(86) PCT No.: PCT/IN2013/000537
§ 371 (c)(1),
(2) Date: Jul. 28, 2014

(87) PCT Pub. No.: WO2014/192006
PCT Pub. Date: Dec. 4, 2014

(65) Prior Publication Data
US 2016/0178525 A1      Jun. 23, 2016

(30) Foreign Application Priority Data
May 27, 2013   (IN) ............................ 2311/CHE/2013

(51) Int. Cl.
*G01J 3/44* (2006.01)
*G01N 21/65* (2006.01)
*G01N 21/51* (2006.01)
*G01N 33/22* (2006.01)

(52) U.S. Cl.
CPC ............. *G01N 21/65* (2013.01); *G01N 21/51* (2013.01); *G01N 33/227* (2013.01); *G01N 2201/063* (2013.01); *G01N 2201/06113* (2013.01)

(58) Field of Classification Search
CPC ... G01J 3/44; G01J 3/02; G01N 21/65; G01N 21/658; G01N 2021/656
USPC .............................................. 356/301, 72–73
See application file for complete search history.

(56) References Cited

U.S. PATENT DOCUMENTS

2008/0268548 A1* 10/2008 Zuckerman .......... G01N 21/658
                                                            436/172
2009/0141271 A1*  6/2009 Matousek .............. A61B 5/417
                                                            356/301

\* cited by examiner

*Primary Examiner* — Abdullahi Nur
(74) *Attorney, Agent, or Firm* — Mark M. Friedman

(57) ABSTRACT

The invention provides a method for detection of hazardous chemicals in a non-metallic container. The method comprises of irradiating the sample at a predefined location with an electromagnetic radiation of specific wavelength; selectively capturing a certain component of the scattered electromagnetic radiation to obtain a plurality of profiles; and filtering the profiles to obtain a signature specific to at least one hazardous chemical present in the container. The invention provides a system for obtaining a signature specific to the hazardous chemicals in the container.

14 Claims, 10 Drawing Sheets

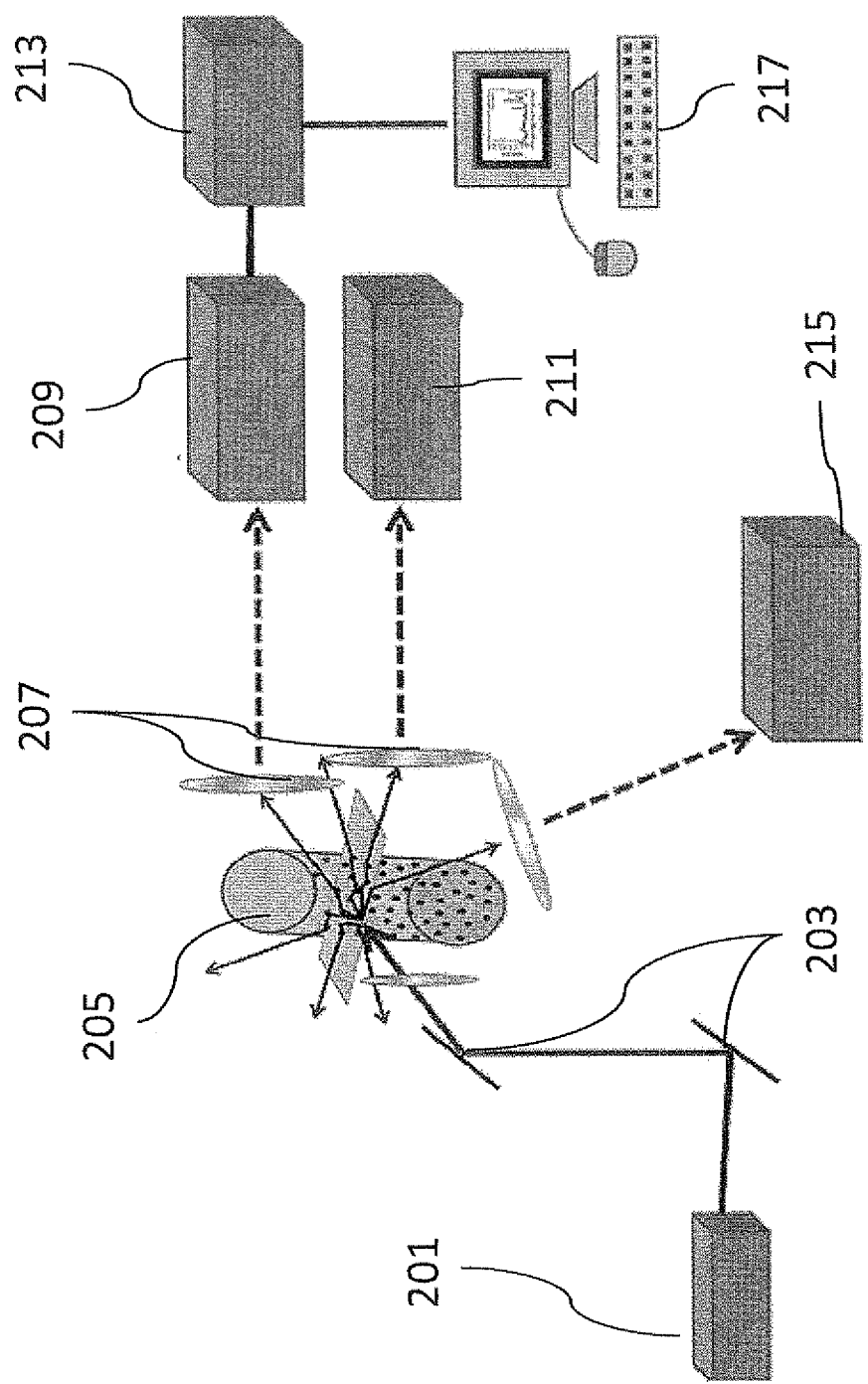

METHOD AND A SYSTEM FOR DETECTION OF HAZARDOUS CHEMICALS IN A NON-METALLIC CONTAINER

FIELD OF INVENTION

The invention generally relates to the field of physical chemistry and particularly to a method and system for detection of hazardous chemicals in a non-metallic container using Raman spectroscopy.

BACKGROUND

Spectroscopic techniques including but not limited to dynamic light scattering, photon correlation spectroscopy and fluorescence correlation spectroscopy have been adopted for studying strongly scattering media such as colloids, gels and tissues. The techniques mentioned above are derived from Rayleigh scattering and/or fluorescence phenomenon. One of the advantages of multiple Rayleigh scattering in strongly scattering media has been the study of dynamics of particles in motion in any given sample. Also the multiple Rayleigh scattering enables estimation of the size distribution of particles in the sample. Another application of Rayleigh scattering has been in areas including but not limited to non-invasive depth profiling and neuro-imaging. However, the scattering profile does not identify the type of materials present in the sample.

Since the multiply scattered light contains both Rayleigh and Raman scattered photons, recording Raman scattered light has been explored for identifying the structure and chemical nature of the molecules. Examples of known techniques that record Raman scattering include but are not limited to Spatially Offset Raman Spectroscopy (SORS), Surface Enhanced Raman Spectroscopy (SERS) and transmission Raman spectroscopy (TRS). SORS works on the principle of backscattering collection geometry wherein the scatterers close to the surface contribute more to the Raman signal than the scatterers located deeper in the sample. SERS works on the principle of Raman light amplification in the presence of a noble metal surface that results in chemical and surface plasmon resonance enhancements of the incident electromagnetic field. One of the primary disadvantages of SORS, SERS and TRS is that the detection is restricted to a specific experimental geometry. For example, SORS works only in the backscattering geometry; SERS relies on metal surface for amplification and TRS cannot distinguish the individual layers of different chemicals in a multi-component layered system. Further, the depth at which detection is effective is limited up to few mm, for example 3 mm. Hence, there is a need for method that can not only identify samples but profile them at various levels of depth.

BRIEF DESCRIPTION OF DRAWINGS

So that the manner in which the recited features of the invention can be understood in detail, some of the embodiments are illustrated in the appended drawings. It is to be noted, however, that the appended drawings illustrate only typical embodiments of this invention and are therefore not to be considered limiting of its scope, for the invention may admit to other equally effective embodiments.

FIG. 2A shows a block diagram of a system for detection of hazardous chemicals in a non-metallic container, according to an embodiment of the invention.

SUMMARY OF THE INVENTION

Figure 1:
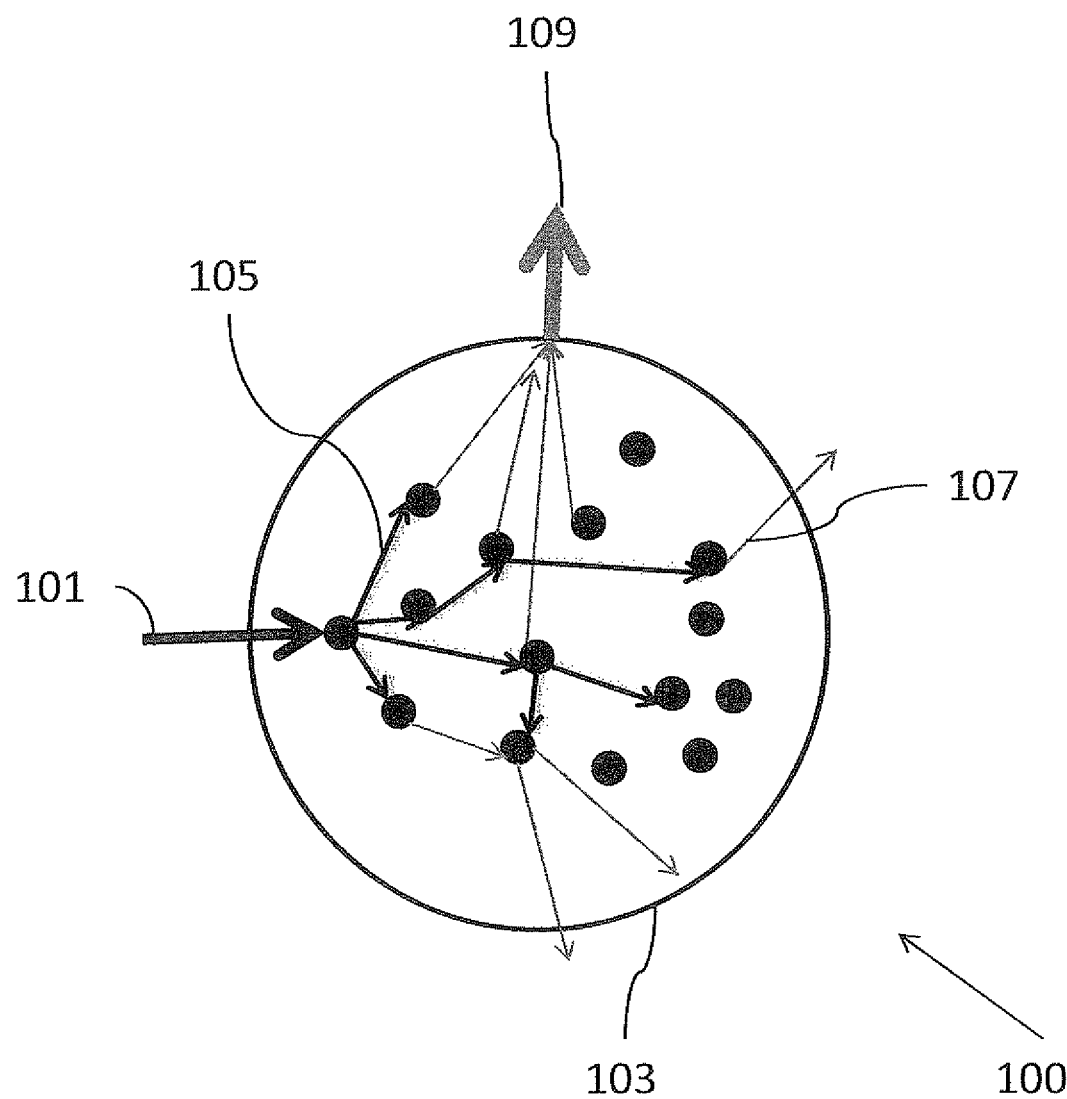
FIG. 1 illustrates the principle of multiple Raman scattering in a non homogenous or homogeneous medium, according to an embodiment of the invention.

One aspect of the invention provides a method for detection of hazardous chemicals in a non-metallic container. The method comprises of irradiating the sample at a predefined location with an electromagnetic radiation of specific wavelength; selectively capturing a certain component of the scattered electromagnetic radiation to obtain a plurality of profiles; and filtering the profiles to obtain a signature specific to at least one hazardous chemical present in the container.

Another aspect of the invention provides a system for detection of the hazardous chemicals in a non-metallic container.

DETAIL DESCRIPTION OF THE INVENTION

Various embodiments of the invention provide a method and a system for detection of hazardous chemicals in a non-metallic container. Examples of hazardous chemicals include but are not limited to potassium perchlorate ($KClO_4$), ammonium nitrate ($NH_4NO_3$), 2,4,6-Trinitrotoluene (TNT), hydrogen peroxide ($H_2O_2$), and nitromethane ($CH_3NO_2$). The method works on the principle of amplification of Raman signal through multiple scattering of light in a randomly distributed medium. The multiply amplified Raman signal enables the method to probe both strongly and weakly scattering media. The multiple scattering can be seen as an amplifying process of Raman light by the medium due to the presence of incident and Rayleigh scattered light. An optical signal corresponding to a particular Raman shift from a molecule can be amplified by subsequent addition of similar Raman photons generated by other similar molecules through multiple scattering due to the presence of incident and Rayleigh scattered photons.

Each particle in a sample is excited by the external electromagnetic field and the resultant field scattered by all other particles. In one embodiment of the invention, the irradiation can be achieved by at least one source of electromagnetic radiation placed at a distance from the sample. The field scattered by the particle depends on the total field to which it is exposed. The light scattered at other positions in the medium contribute to the irradiance at a position of observation. Therefore, the scattered light merely changes direction and is lost from a beam propagating in a particular direction, but contributes to other directions. When there are many particles and their separation is random, the scattered field will be incoherent, i.e., there is no systematic relation among the phases of the waves scattered by the individual particles. Thus, the total irradiance scattered by the collection in any direction is the sum of the irradiances scattered by the individual particles in that direction. The total signal observed at any point of observation is dependent on the scattering cross section, the number density of particles and the medium thickness. Therefore, amplified Raman signal can enable us to probe dense media of thickness exceeding a few tens of mm and probe samples buried deep inside them. Since Raman signals obtained are specific to the scatter of the source, accurate profiling of substances, to obtain chemical signatures specific to at least one hazardous chemical is possible irrespective of the extent to which the source is scattered. The signatures obtained includes but is not limited to spectral graphs, images and all such depictions capable of identifying the hazardous chemical inside the container.

FIG. 1 illustrates the principle of multiple Raman scattering in a non homogenous medium, according to an embodiment of the invention. A monochromatic coherent source of light 101 is incident on a non homogenous sample 103. The incident light 101 is scattered by the sample 103. The scattered light includes both elastic (Rayleigh) 105 and inelastic (Raman) scattering 107. The inelastic or the Raman scattered light can emerge out of the sample at multiple directions due to multiple continuous scattering. The diagram shows one such situation where Raman photons add up in certain directions due to sequential scattering events, resulting in a detectable signal 109.

FIG. 2A shows a block diagram of a system for detection of hazardous chemicals in a non-metallic container, according to an embodiment of the invention. The system includes a source of electromagnetic radiation 201. A lens arrangement 203 focuses the source 201 onto a non homogenous or homogeneous sample 205. A plurality of collection lenses 207 are placed at various locations around the sample 205. The collection lenses 207 focuses the scattered Raman photons onto a spectrometer 209. A detector 213 is coupled to the spectrometer 209. The output of the detector 213 is sent to an analysis unit 217 for estimating various parameters.

In one embodiment of the invention, the electromagnetic radiation is a monochromatic coherent source of light. Different wavelength excitation source in the range of 500 nm to 1400 nm can be used for these experiments. The spectral range is dependent on the spectrometer and the detector and the penetration depth depend upon on the selection of the source wavelength. In one example of the invention, the wavelength of the source of light for excitation is chosen in the IR region. The 830 nm laser is preferred over visible light for investigating strongly scattering media in order to avoid fluorescence and absorption, and to attain a better penetration depth. The laser beam is focused onto the sample using an optical directing element. The optical directing element is selected from a group including but not limited to lens, mirrors and a combination thereof. In an example of the invention a plano-convex lens is used as an optical directing element. In an alternate embodiment of the invention, the sample can be irradiated directly from the electromagnetic source. The incident beam polarization is perpendicular to the plane of observation of the scattered light. The Raman signals are collected from the samples using a 50-mm diameter biconvex lens (f/4.14) and imaged onto the spectrometer slit with a magnification of 2. The f-number matching between the collection lens and the spectrometer is achieved through appropriate optics. The spectrometer entrance slit is adjusted to obtain the best spectral resolution possible. Laser line filters such as notch filters, are used in front of the entrance slit to eliminate the Rayleigh scattered light.

Figure 2B:
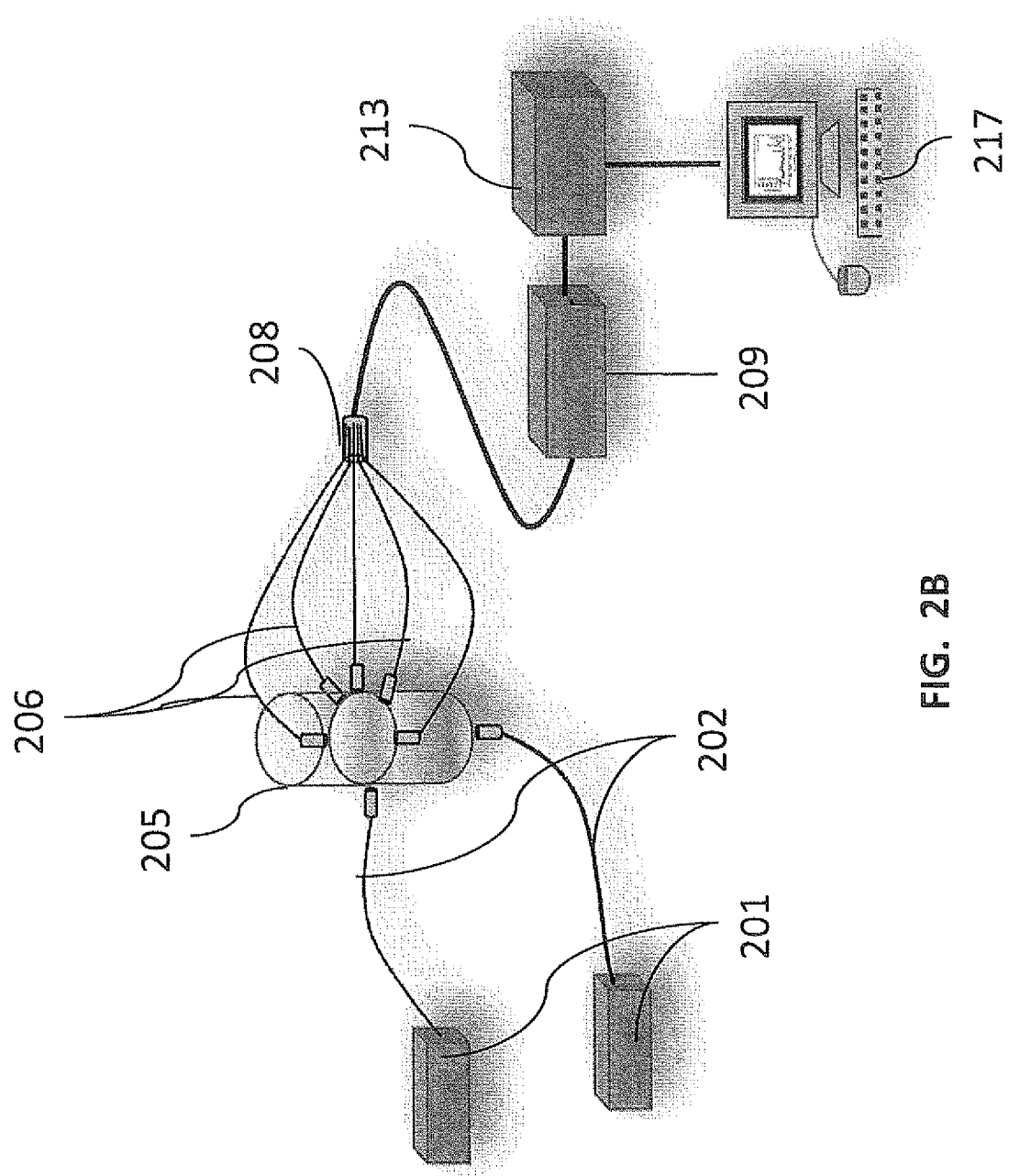
FIG. 2B shows an arrangement for multipoint detection of hazardous chemicals in a non-metallic container, according to an alternate embodiment of the invention.

FIG. 2B shows an arrangement for multipoint detection of hazardous chemicals in a non metallic container, according to an alternate embodiment of the invention. The laser beam from a source 201 is delivered through an optical fiber 202 to the sample 205. The Raman signals are collected using a plurality of fibers 206 attached to the sample container 205 at varying angles with respect to the incident beam. The fibers 206 are bundled and placed in front of collection optics arrangement 208 fixed to the entrance slit of the spectrometer 209.

The system as described herein is used for detecting hazardous chemicals in a non metallic container. The hazardous chemicals can be detected from specific signatures that can be obtained from the container independent of the collection geometry. The collection geometry as referred herein means orientation and position of the collection arrangement. The collection arrangement includes but is not limited to lenses, fiber optics and all such devices capable of capturing the scattered electromagnetic radiation, as obvious to a person skilled in the art, from the sample. Experiments were performed for non-invasive and non destructive detection and/or screening of hazardous chemicals packed in different types of transparent, translucent and opaque containers. Examples of containers include but are not limited to commercial high density polyethylene (HDPE) containers; glass bottles, envelopes, plastic covers, plastic tubes and all such containers capable of holding solid and/or fluid samples.

Figure 3:
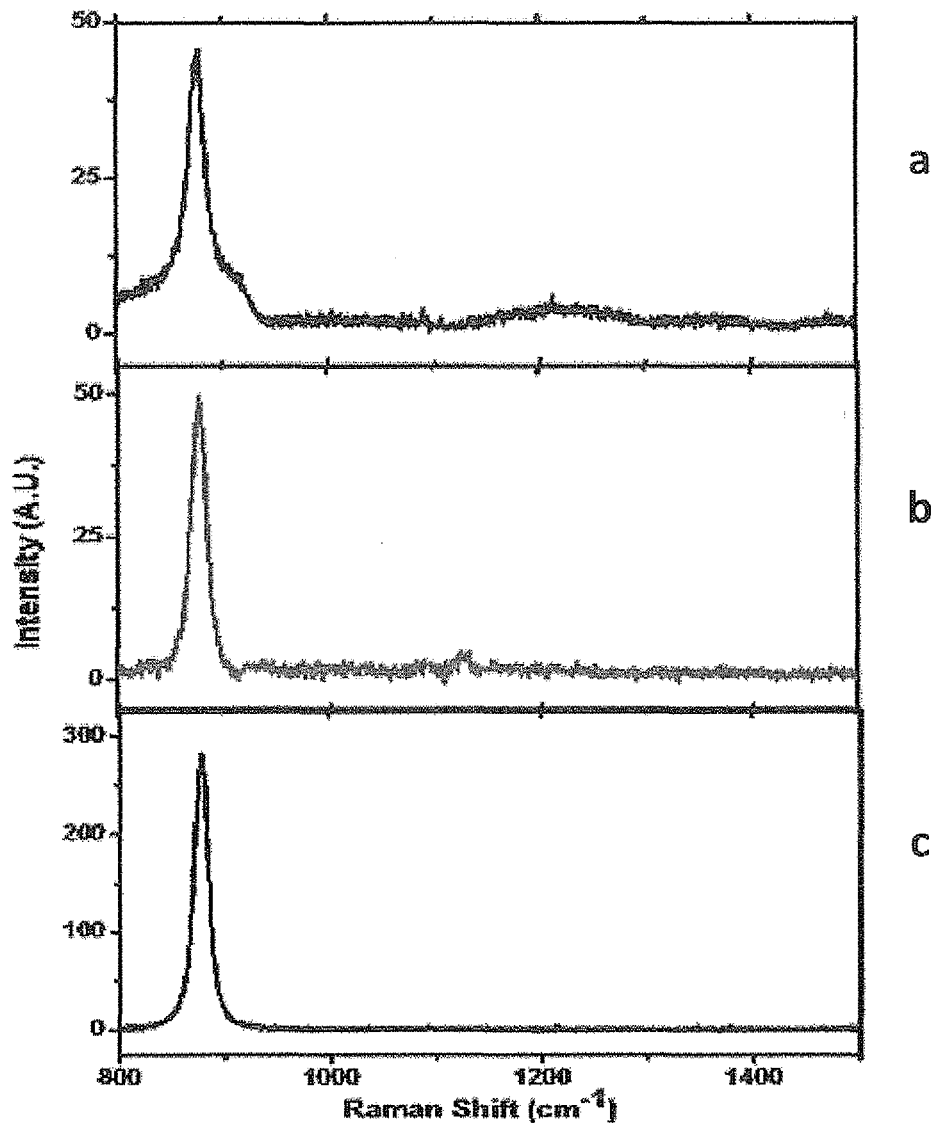
FIG. 3 shows specific detection of $H_2O_2$ through different colored bottle, according to an embodiment of the invention.

FIG. 3 shows specific detection of $H_2O_2$ through different colored bottles, according to an embodiment of the invention. Three instances of colored bottles were chosen, a) a brown beer bottle; b) a green beer bottle and c) a colored PET bottle. It can be noted that the 876 $cm^{-1}$ peak for O-O vibrational stretch in $H_2O_2$ is clearly observed in all the cases.

Figure 4:
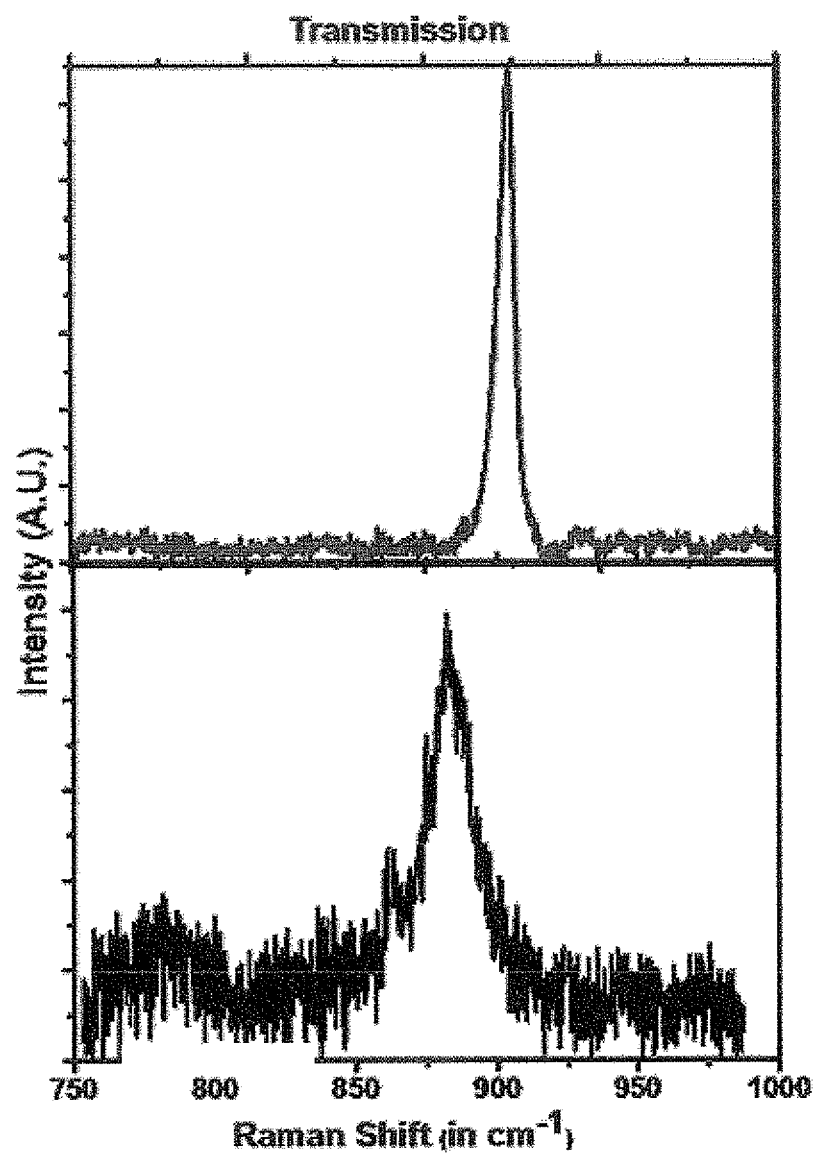
FIG. 4 shows specific detection of a) $CH_3NO_2$ and b) $NH_4NO_3$ in HDPE container of a defined thickness, as detected through a transmission mode, according to an embodiment of the invention.

FIG. 4 shows specific detection of a) $CH_3NO_2$ and b) $NH_4NO_3$ in HDPE container of a defined thickness, as detected through a transmission mode, according to an embodiment of the invention.

Figure 5:
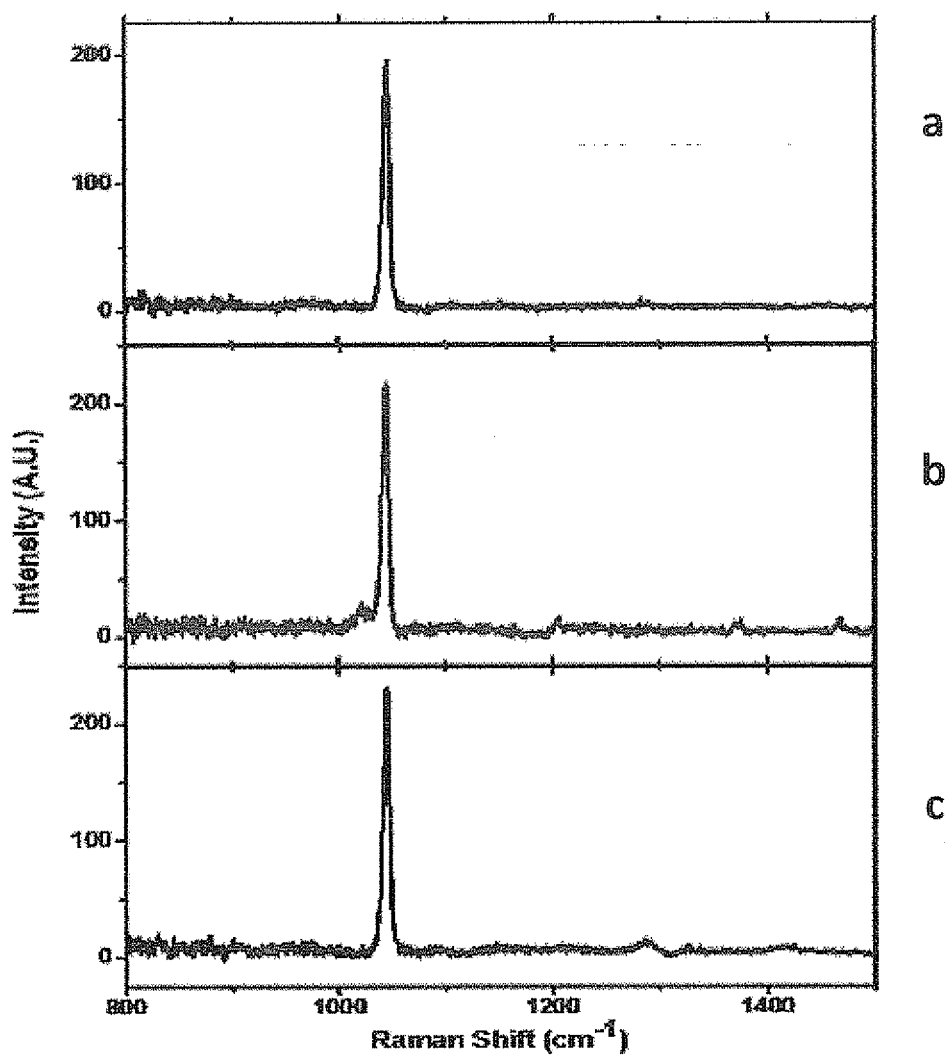
FIG. 5 shows specific detection of $NH_4NO_3$ in a) a white, b) a brown and c) a green envelope, as detected through reflection mode geometry, according to an embodiment of the invention.

FIG. 5 shows specific detection of $NH_4NO_3$ in a) a white, b) a brown and c) a green envelope, as detected through reflection mode geometry, according to an embodiment of the invention.

Figure 6:
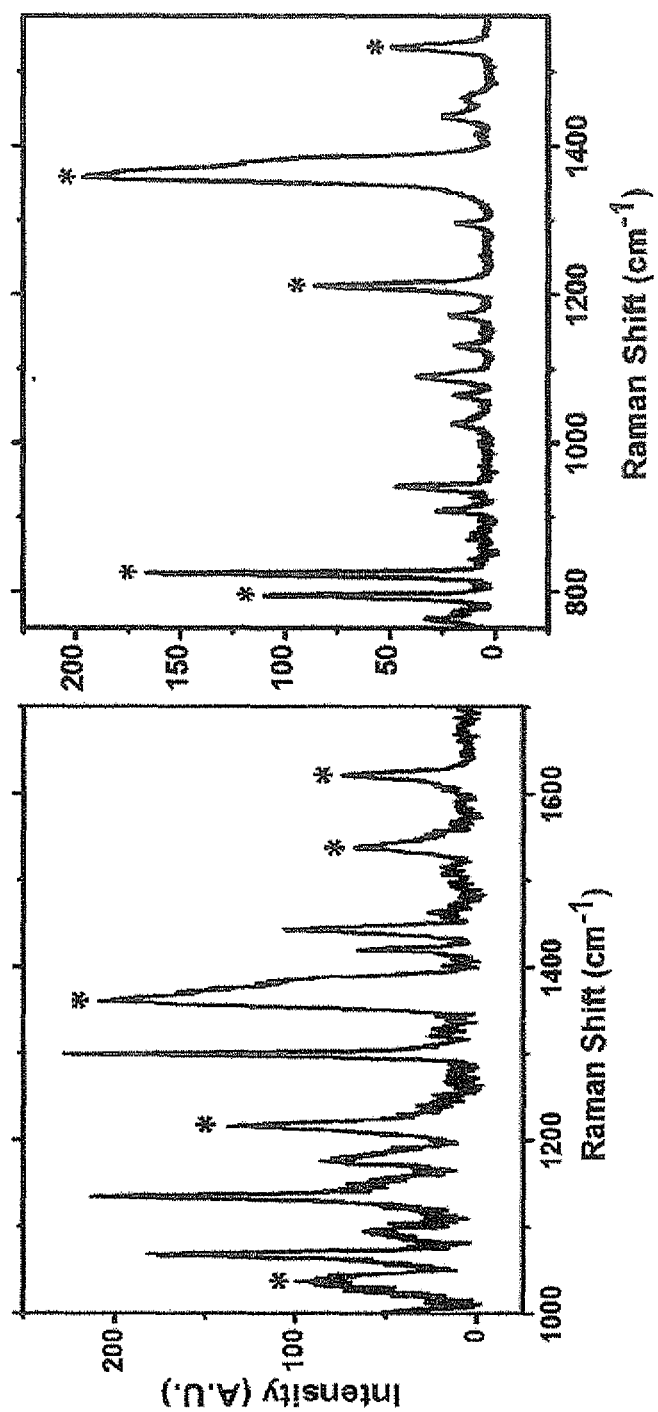
FIG. 6 shows specific detection of 2,4,6-Trinitrotoluene (TNT) in a translucent HDPE container, as detected through a) a reflection geometry, and b) a transmission geometry, according to an embodiment of the invention.

FIG. 6 shows specific detection of 2,4,6-Trinitrotoluene (TNT) in a translucent HDPE container, as detected through a) a reflection geometry, and b) a transmission geometry, according to an embodiment of the invention.

Figure 7:
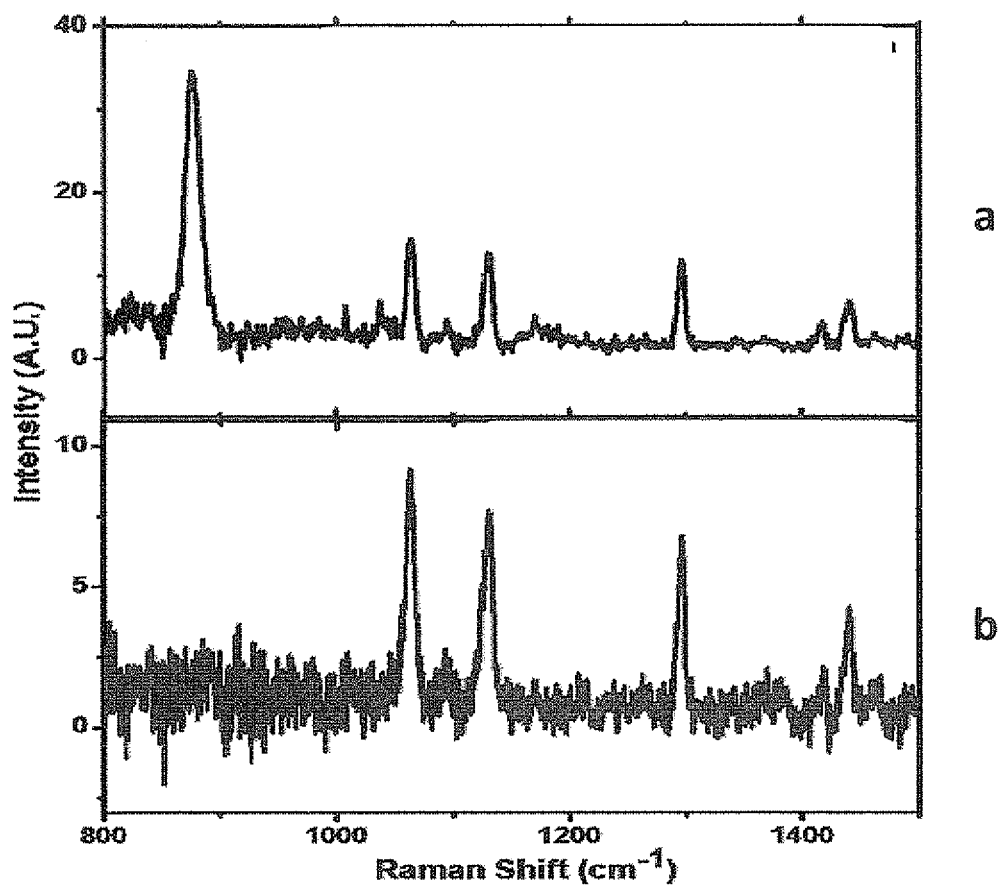
FIG. 7 shows specific detection, of $H_2O_2$, mixed with a cream and concealed in commercial HDPE bottle, as detected through transmission geometry, according to an embodiment of the invention.

FIG. 7 shows specific detection, of $H_2O_2$, mixed with a cream and concealed in commercial HDPE bottle, as detected through transmission geometry, according to an embodiment of the invention. The signature obtained is compared with the signature for a typical innocuous material like commercial body lotion.

Figure 8:
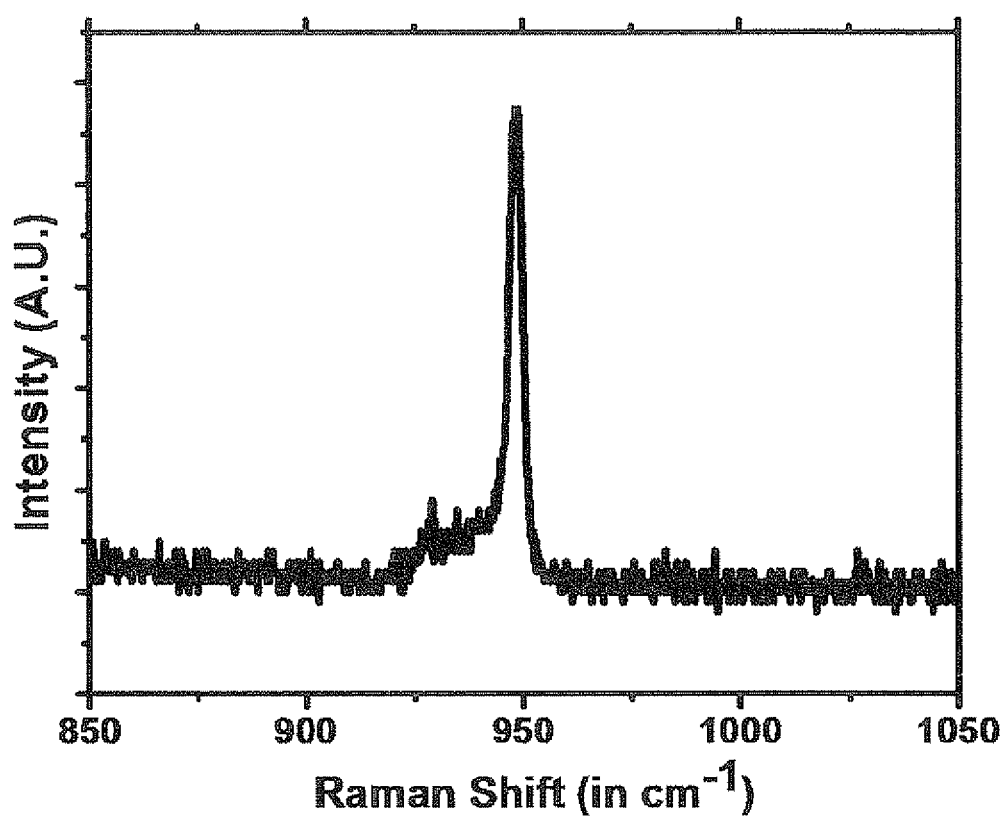
FIG. 8 shows specific detection of $KClO_4$ in HDPE container using optical fibers, according to an alternate embodiment of the invention.

FIG. 8 shows specific detection of KClO$_4$ in HDPE container using optical fibers, according to an alternate embodiment of the invention.

Figure 9:
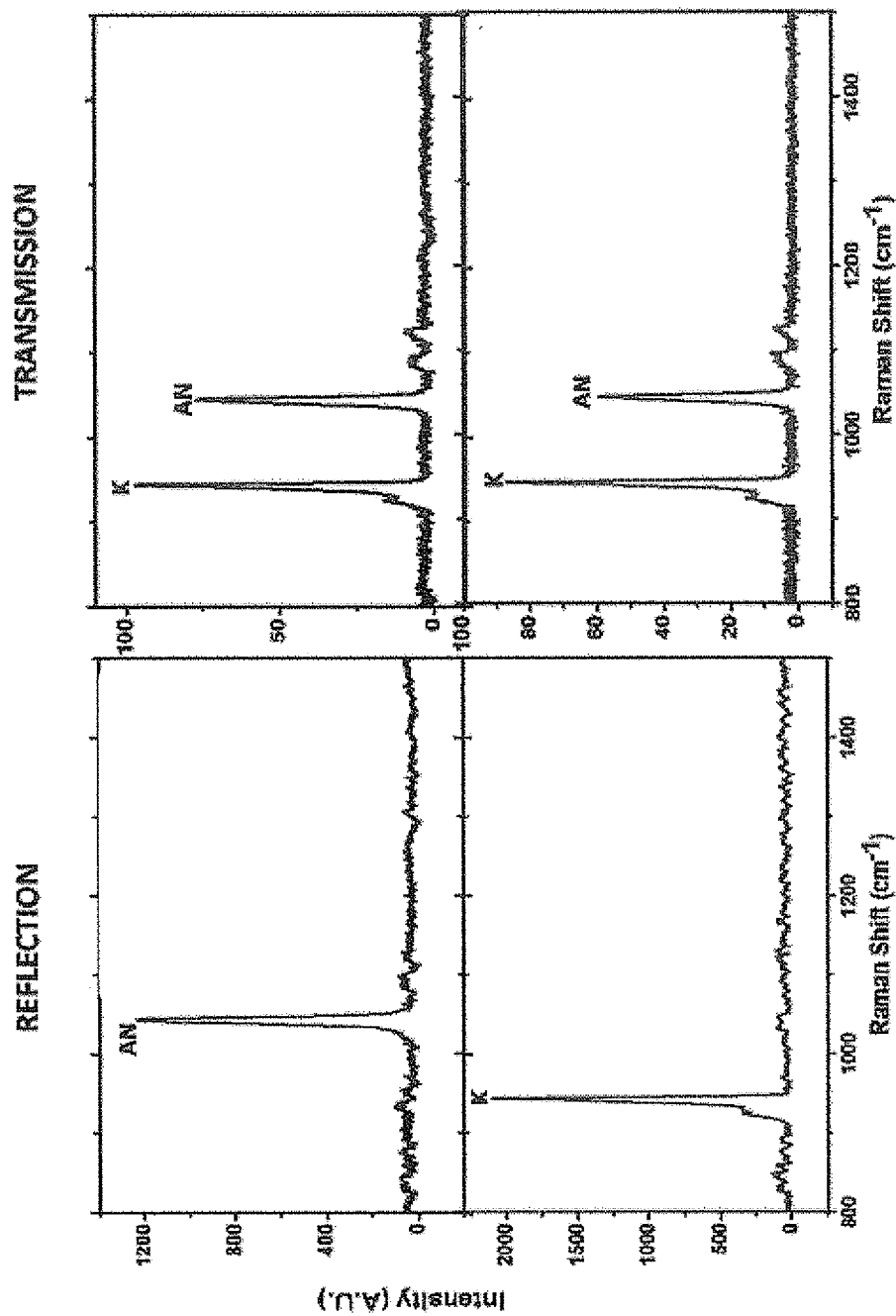
FIG. 9 shows specific detection of a mixture of explosives $KClO_4$ contained in a multilayer container as detected through a) a reflection mode and b) a transmission mode, according to an embodiment of the invention.

FIG. 9 shows specific detection of a mixture of explosives KClO$_4$ contained in a multilayer container as detected through a) a reflection mode and b) a transmission mode, according to an embodiment of the invention. The experiment was conducted on thick explosive layers. Further the explosive layers were concealed within a multilayer container. In one example of the invention the multilayer container was constructed by wrapping the explosive layer in a plastic bag and concealing the plastic bag inside an envelope. The experiment could be done in geometries such as backscattering, sideways and transmission. It is interesting to note that in transmission geometry, the signal containing peaks from both the layers are identified, whereas in backscattering geometry the Raman signal only for the layer facing the input laser beam is identified; the signal from the second layer is obtained only by flipping the second layer to face the laser beam.

The invention as described herein provides a method and an system for detection of hazardous chemicals in a non-metallic container. The method predominantly utilizes a Raman spectroscopic technique that is geometry independent. The spectroscopic technique is capable of probing any type of scattering samples and identifies individual layers in a multilayer system. One of the primary advantages of the method and the system described herein is that the method is independent of the experimental geometry. The non dependence on the geometry enables collection of Raman signals from samples lying within other scattering materials for example, a dense plastic container, using either conventional lenses and/or optical fibers placed at different positions around the sample. The technique basically depends on recording multiply amplified Raman signal of target materials coming out in all directions. Further, the technique as described herein is a portable device which can be a potential tool for non-invasive and non destructive detection or screening of hazardous chemicals packed in different types of transparent, translucent and opaque containers.

The foregoing description of the invention has been set for merely to illustrate the invention and is not intended to be limiting. Since modifications of the disclosed embodiments incorporating the spirit and substance of the invention may occur to person skilled in the art, the invention should be construed to include everything within the scope of the appended claims and equivalents thereof.

We claim:

1. A method for detection of hazardous chemicals in a non-metallic container, the method comprising:
    irradiating the container at a predefined location with an electromagnetic radiation of specific wavelength;
    selectively capturing a certain component of the scattered electromagnetic radiation at any of observation to obtain from a cross section of said radiation a plurality of profiles; and
    filtering the profiles to obtain a signature specific to at least one hazardous chemical present in the container.

2. The method according to claim 1, wherein the predefined location is at least one position around the container.

3. The method according to claim 1, wherein the wavelength of the electromagnetic radiation is in the range of 500 nm to 1400 nm.

4. The method according to claim 1, wherein the component of the scattered electromagnetic radiation is a multiply amplified Raman scattering.

5. The method according to claim 1, wherein the selective capturing of the scattered electromagnetic radiation is independent of collection angle.

6. The method according to claim 1, wherein the captured electromagnetic radiation is an amplified scattering obtained through multiple scattering of the incident electromagnetic radiation.

7. The method according to claim 1, wherein the method is capable of detecting hazardous chemicals at a depth of at least 5 mm inside the container.

8. A system for detection of hazardous chemicals in a non-metallic container, the system comprising:
    at least one electromagnetic radiation source;
    a first arrangement for directing the electromagnetic radiation onto the container;
    a second arrangement for collecting the scattered electromagnetic radiation from the sample;
    a spectrum analyzer operably coupled to the second arrangement; and
    a detector connected to the optical spectrum analyzer and being configured to selectively capture a certain component of said scattered electromagnetic radiation at any point of observation to obtain from a cross section of said radiation a plurality of profiles.

9. The system according to claim 8, wherein the first arrangement comprises of:
    at least one optical fiber connected to the source; and
    at least one directing optical element comprising of lens, mirror and a combination thereof wherein the directing element is positioned to direct the electromagnetic radiation onto the sample.

10. The system according to claim 8, wherein the second arrangement is a plurality of optical elements positioned to direct the scattered electromagnetic radiation to the spectrum analyzer.

11. The system according to claim 8, wherein the positioning of the second arrangement is independent of the orientation and/or position of the arrangement at the sample.

12. The system according to claim 8, wherein the second arrangement is a plurality of optical fibers positioned at various locations on the sample for directing the scattered electromagnetic radiation onto the spectrum analyzer.

13. The system according to claim 8, wherein the analyzer comprises of
    a spectrometer;
    a filter for selectively capturing the scattered electromagnetic radiation; and
    an analysis unit for obtaining profile of the hazardous chemical.

14. The system according to claim 8, wherein the system is capable of detecting hazardous chemicals at any point of need location.

* * * * *